(12) United States Patent
Ball

(10) Patent No.: US 12,310,857 B2
(45) Date of Patent: May 27, 2025

(54) TOTAL SHOULDER PROSTHESIS HAVING INSET GLENOID IMPLANT CONVERTIBLE FROM ANATOMIC TO REVERSE

(71) Applicant: SHOULDER INNOVATIONS, INC., Holland, MI (US)

(72) Inventor: Robert J. Ball, Holland, MI (US)

(73) Assignee: Shoulder Innovations, Inc., Grand Rapids, MI (US)

( * ) Notice: Subject to any disclaimer, the term of this patent is extended or adjusted under 35 U.S.C. 154(b) by 804 days.

(21) Appl. No.: 17/379,894

(22) Filed: Jul. 19, 2021

(65) Prior Publication Data

US 2021/0338446 A1     Nov. 4, 2021

Related U.S. Application Data

(63) Continuation of application No. 15/952,063, filed on Apr. 12, 2018, now Pat. No. 11,065,125.

(Continued)

(51) Int. Cl.
*A61F 2/40*          (2006.01)
*A61B 17/17*        (2006.01)
(Continued)

(52) U.S. Cl.
CPC ........ *A61F 2/4081* (2013.01); *A61B 17/1778* (2016.11); *A61F 2/30767* (2013.01); *A61F 2002/302* (2013.01); *A61F 2002/30331* (2013.01); *A61F 2002/30367* (2013.01); *A61F 2002/305* (2013.01); *A61F 2002/30607* (2013.01); *A61F 2002/3069* (2013.01); *A61F 2002/30878* (2013.01);
(Continued)

(58) Field of Classification Search
CPC ..... A61F 2/4081; A61F 2/5059; A61F 2/4612
See application file for complete search history.

(56) References Cited

U.S. PATENT DOCUMENTS

| 2,781,758 A | 2/1957 | Jacques |
| 3,979,778 A | 9/1976 | Stroot |

(Continued)

FOREIGN PATENT DOCUMENTS

| AU | 2018251815 | 3/2024 |
| DE | 4220217 | 12/1993 |

(Continued)

OTHER PUBLICATIONS

U.S. Appl. No. 16/701,118, filed Dec. 2, 2019, Gunther.
(Continued)

*Primary Examiner* — Brian A Dukert
(74) *Attorney, Agent, or Firm* — Knobbe Martens Olson & Bear, LLP

(57) ABSTRACT

Disclosed are prosthesis systems and methods that provide ways by which the articulating surfaces of the implant can be exchanged such that the anatomic surfaces can be converted to reverse surfaces, while not exchanging the fixation components. Also disclosed herein are methods by which the surgeon can implant an inset anatomic articulating glenoid implant whereby at a later date, can remove the anatomic articulating surface and replace it with a reverse articulating surface such that the primary means of fixation remains well fixed in the glenoid fossa at the moment of articular exchange.

17 Claims, 20 Drawing Sheets

Related U.S. Application Data

(60) Provisional application No. 62/485,839, filed on Apr. 14, 2017.

(51) Int. Cl.
  *A61F 2/30* (2006.01)
  *A61F 2/46* (2006.01)

(52) U.S. Cl.
  CPC ... *A61F 2002/30901* (2013.01); *A61F 2/4059* (2013.01); *A61F 2002/4085* (2013.01); *A61F 2/4612* (2013.01); *A61F 2310/00011* (2013.01)

(56) References Cited

U.S. PATENT DOCUMENTS

| | | | |
|---|---|---|---|
| 4,003,095 A | 1/1977 | Gristina | |
| 4,012,796 A | 3/1977 | Weisman et al. | |
| 4,045,826 A | 9/1977 | Stroot | |
| 4,206,517 A | 6/1980 | Pappas et al. | |
| 4,261,062 A | 4/1981 | Amstutz et al. | |
| 4,404,693 A | 9/1983 | Zweymuller | |
| 4,550,450 A | 11/1985 | Kinnett | |
| 4,698,063 A | 10/1987 | Link et al. | |
| 4,700,660 A | 10/1987 | Levchenko et al. | |
| 4,783,192 A | 1/1988 | Wroblewski et al. | |
| 4,827,919 A | 5/1989 | Barbarito et al. | |
| 4,865,605 A | 9/1989 | Dines et al. | |
| 4,908,036 A | 3/1990 | Link et al. | |
| 4,964,865 A | 10/1990 | Burkhead et al. | |
| 4,986,833 A | 1/1991 | Worland | |
| 4,990,161 A | 2/1991 | Kampner | |
| 5,030,219 A | 7/1991 | Matsen, III et al. | |
| 5,032,132 A | 7/1991 | Matsen, III et al. | |
| 5,080,673 A | 1/1992 | Burkhead et al. | |
| 5,108,440 A | 4/1992 | Grundei | |
| 5,281,226 A | 1/1994 | Davydov et al. | |
| 5,282,865 A | 2/1994 | Dong | |
| 5,314,479 A | 5/1994 | Rockwood, Jr. et al. | |
| 5,314,489 A | 5/1994 | Hoffman et al. | |
| 5,344,458 A | 9/1994 | Bonutti | |
| 5,358,525 A | 10/1994 | Fox et al. | |
| 5,370,694 A | 12/1994 | Davidson | |
| 5,437,677 A | 8/1995 | Shearer et al. | |
| 5,462,563 A | 10/1995 | Shearer et al. | |
| 5,480,450 A | 1/1996 | James et al. | |
| 5,489,309 A | 2/1996 | Lackey et al. | |
| 5,489,310 A | 2/1996 | Mikhail | |
| 5,507,748 A | 4/1996 | Sheehan et al. | |
| 5,507,819 A | 4/1996 | Wolf | |
| 5,514,184 A | 5/1996 | Doi | |
| 5,549,683 A | 8/1996 | Bonutti | |
| 5,593,448 A | 1/1997 | Dong | |
| 5,702,447 A | 12/1997 | Walch et al. | |
| 5,702,486 A | 12/1997 | Craig et al. | |
| 5,746,771 A | 5/1998 | Clement, Jr. et al. | |
| 5,755,811 A | 5/1998 | Tanamal et al. | |
| 5,769,856 A | 6/1998 | Dong et al. | |
| 5,800,551 A | 9/1998 | Williamson et al. | |
| 5,928,285 A | 7/1999 | Bigliani et al. | |
| 6,019,766 A | 2/2000 | Ling et al. | |
| 6,037,724 A | 3/2000 | Buss et al. | |
| 6,228,119 B1 | 5/2001 | Ondria et al. | |
| 6,231,913 B1 | 5/2001 | Schwimmer et al. | |
| 6,290,726 B1 | 9/2001 | Pope et al. | |
| 6,334,874 B1 | 1/2002 | Tornier et al. | |
| 6,364,910 B1 | 4/2002 | Shultz et al. | |
| 6,368,353 B1 | 4/2002 | Arcand | |
| 6,379,386 B1 | 4/2002 | Resch et al. | |
| 6,458,136 B1 | 10/2002 | Allard et al. | |
| 6,514,287 B2 | 2/2003 | Ondria et al. | |
| 6,520,964 B2 | 2/2003 | Tallarida et al. | |
| 6,589,281 B2 | 7/2003 | Hyde, Jr. | |
| 6,610,067 B2 | 8/2003 | Tallarida et al. | |
| 6,620,197 B2 | 9/2003 | Maroney | |
| 6,673,115 B2 | 1/2004 | Resch et al. | |
| 6,679,916 B1 | 1/2004 | Frankle et al. | |
| 6,679,917 B2 | 1/2004 | Ek | |
| 6,699,289 B2 | 3/2004 | Iannotti et al. | |
| 6,709,463 B1 | 3/2004 | Pope et al. | |
| 6,712,823 B2 | 3/2004 | Grusin et al. | |
| 6,761,740 B2 | 7/2004 | Tornier | |
| 6,783,549 B1 | 8/2004 | Stone et al. | |
| 6,875,234 B2 | 4/2005 | Lipman et al. | |
| 6,953,478 B2 | 10/2005 | Bouttens et al. | |
| 7,011,686 B2 | 3/2006 | Ball et al. | |
| 7,044,973 B2 | 5/2006 | Rockwood et al. | |
| 7,238,089 B2 | 7/2007 | Tsumuraya et al. | |
| 7,238,208 B2 | 7/2007 | Camino et al. | |
| 7,261,741 B2 | 8/2007 | Weisman et al. | |
| 7,294,149 B2 | 11/2007 | Hozack et al. | |
| 7,320,709 B2 | 1/2008 | Felt et al. | |
| 7,329,284 B2 | 2/2008 | Maroney et al. | |
| 7,465,319 B2 | 12/2008 | Tornier | |
| 7,517,364 B2 | 4/2009 | Long et al. | |
| 7,618,462 B2 | 11/2009 | Ek | |
| 7,678,151 B2 | 3/2010 | Ek | |
| 7,749,278 B2 | 7/2010 | Frederick et al. | |
| 7,753,959 B2 | 7/2010 | Berelsman et al. | |
| 7,766,969 B2 | 8/2010 | Justin et al. | |
| 7,776,098 B2 | 8/2010 | Murphy | |
| 7,892,287 B2 | 2/2011 | Deffenbaugh | |
| 7,922,769 B2 | 4/2011 | Deffenbaugh et al. | |
| 8,007,538 B2 | 8/2011 | Gunther | |
| 8,038,719 B2 | 10/2011 | Gunther | |
| 8,048,161 B2 | 11/2011 | Guederian et al. | |
| 8,048,167 B2 | 11/2011 | Dietz et al. | |
| 8,303,665 B2 | 11/2012 | Tornier et al. | |
| 8,529,629 B2 | 9/2013 | Angibaud et al. | |
| 8,608,805 B2 | 12/2013 | Forrer et al. | |
| 8,721,726 B2 | 5/2014 | Capon et al. | |
| 8,778,028 B2 | 7/2014 | Gunther et al. | |
| 8,840,671 B2 | 9/2014 | Ambacher | |
| 8,920,508 B2 | 12/2014 | Iannotti et al. | |
| 8,940,054 B2 | 1/2015 | Wiley et al. | |
| 9,114,017 B2 | 8/2015 | Lappin | |
| 9,283,083 B2 | 3/2016 | Winslow et al. | |
| 9,381,086 B2 | 7/2016 | Ries et al. | |
| 9,498,345 B2 * | 11/2016 | Burkhead, Jr. | A61F 2/4081 |
| 9,545,311 B2 | 1/2017 | Courtney, Jr. et al. | |
| 9,545,312 B2 | 1/2017 | Tornier et al. | |
| 9,610,166 B2 | 4/2017 | Gunther et al. | |
| 9,615,839 B2 | 4/2017 | Olson | |
| 9,693,784 B2 | 7/2017 | Gunther | |
| 9,867,710 B2 | 1/2018 | Dalla Pria et al. | |
| 10,034,753 B2 | 7/2018 | Dressler et al. | |
| 10,143,559 B2 | 12/2018 | Ries et al. | |
| 10,357,373 B2 | 7/2019 | Gargac et al. | |
| 10,492,926 B1 | 12/2019 | Gunther | |
| 10,702,390 B2 | 7/2020 | Chavarria et al. | |
| 10,779,952 B2 | 9/2020 | Gunther et al. | |
| 10,786,265 B2 | 9/2020 | Gunther | |
| 10,925,745 B2 | 2/2021 | Cardon et al. | |
| 10,966,788 B2 | 4/2021 | Britton et al. | |
| 11,065,125 B2 | 7/2021 | Ball | |
| 11,464,645 B2 | 10/2022 | Cardon et al. | |
| D977,643 S | 2/2023 | Ball et al. | |
| 11,696,772 B2 | 7/2023 | Gunther | |
| 11,771,561 B2 | 10/2023 | Running et al. | |
| 2001/0011192 A1 | 8/2001 | Ondria et al. | |
| 2001/0037153 A1 | 11/2001 | Rockwood, Jr. et al. | |
| 2001/0047210 A1 | 11/2001 | Wolf | |
| 2002/0082702 A1 | 6/2002 | Resch et al. | |
| 2002/0087213 A1 | 7/2002 | Bertram, III | |
| 2002/0095214 A1 | 7/2002 | Hyde, Jr. | |
| 2002/0111689 A1 | 8/2002 | Hyde, Jr. et al. | |
| 2002/0138148 A1 | 9/2002 | Hyde, Jr. et al. | |
| 2003/0033019 A1 | 2/2003 | Lob | |
| 2003/0100952 A1 | 5/2003 | Rockwood, Jr. et al. | |
| 2003/0114933 A1 | 6/2003 | Bouttens et al. | |
| 2003/0144738 A1 | 7/2003 | Rogalski | |
| 2003/0158605 A1 | 8/2003 | Tournier | |
| 2003/0163202 A1 | 8/2003 | Lakin | |
| 2003/0236572 A1 | 12/2003 | Bertram, III | |
| 2004/0002766 A1 | 1/2004 | Hunter et al. | |

(56) References Cited

U.S. PATENT DOCUMENTS

| | | |
|---|---|---|
| 2004/0039449 A1 | 2/2004 | Tournier |
| 2004/0039451 A1 | 2/2004 | Southworth |
| 2004/0059424 A1 | 3/2004 | Guederian et al. |
| 2004/0064187 A1 | 4/2004 | Ball et al. |
| 2004/0064189 A1 | 4/2004 | Maroney et al. |
| 2004/0064190 A1 | 4/2004 | Ball et al. |
| 2004/0107002 A1 | 6/2004 | Katsuya |
| 2004/0122519 A1 | 6/2004 | Wiley et al. |
| 2004/0122520 A1 | 6/2004 | Lipman et al. |
| 2004/0167629 A1 | 8/2004 | Geremakis et al. |
| 2004/0167630 A1 | 8/2004 | Rolston |
| 2004/0193168 A1 | 9/2004 | Long et al. |
| 2004/0193275 A1 | 9/2004 | Long et al. |
| 2004/0193276 A1 | 9/2004 | Maroney et al. |
| 2004/0193277 A1 | 9/2004 | Long et al. |
| 2004/0193278 A1 | 9/2004 | Maroney et al. |
| 2004/0199260 A1 | 10/2004 | Pope et al. |
| 2004/0220674 A1 | 11/2004 | Pria |
| 2004/0230311 A1 | 11/2004 | Cyprien et al. |
| 2004/0260398 A1 | 12/2004 | Kelman |
| 2005/0043805 A1 | 2/2005 | Chudik |
| 2005/0049709 A1 | 3/2005 | Tornier |
| 2005/0065612 A1 | 3/2005 | Winslow |
| 2005/0075638 A1 | 4/2005 | Collazo |
| 2005/0107882 A1 | 5/2005 | Stone et al. |
| 2005/0119531 A1 | 6/2005 | Sharratt |
| 2005/0177241 A1 | 8/2005 | Angibaud et al. |
| 2005/0261775 A1 | 11/2005 | Baum et al. |
| 2005/0278030 A1 | 12/2005 | Tornier et al. |
| 2006/0036328 A1 | 2/2006 | Parrott et al. |
| 2006/0069443 A1 | 3/2006 | Deffenbaugh et al. |
| 2006/0069444 A1 | 3/2006 | Deffenbaugh et al. |
| 2006/0069445 A1 | 3/2006 | Ondrla et al. |
| 2006/0200249 A1 | 9/2006 | Beguin et al. |
| 2007/0038302 A1 | 2/2007 | Shultz et al. |
| 2007/0050042 A1 | 3/2007 | Dietz et al. |
| 2007/0055380 A1 | 3/2007 | Berelsman et al. |
| 2007/0112433 A1 | 5/2007 | Frederick et al. |
| 2007/0118229 A1 | 5/2007 | Bergin et al. |
| 2007/0156246 A1 | 7/2007 | Meswania et al. |
| 2007/0179624 A1 | 8/2007 | Stone et al. |
| 2007/0225817 A1 | 9/2007 | Ruebelt et al. |
| 2007/0225818 A1 | 9/2007 | Reubelt et al. |
| 2008/0021564 A1 | 1/2008 | Gunther |
| 2008/0082175 A1 | 4/2008 | Holovacs et al. |
| 2008/0177327 A1 | 7/2008 | Malandain et al. |
| 2008/0234820 A1 | 9/2008 | Felt et al. |
| 2008/0294268 A1 | 11/2008 | Baum et al. |
| 2009/0105837 A1 | 4/2009 | LaFosse et al. |
| 2009/0125113 A1 | 5/2009 | Guederian et al. |
| 2009/0228112 A1 | 9/2009 | Clark et al. |
| 2009/0270866 A1 | 10/2009 | Poncet |
| 2009/0281630 A1 | 11/2009 | Delince et al. |
| 2009/0287309 A1 | 11/2009 | Walch et al. |
| 2010/0049327 A1* | 2/2010 | Isch .......................... A61F 2/34 623/19.12 |
| 2010/0087876 A1 | 4/2010 | Gunther |
| 2010/0087877 A1 | 4/2010 | Gunther |
| 2010/0114326 A1 | 5/2010 | Winslow et al. |
| 2010/0161066 A1 | 6/2010 | Iannotti et al. |
| 2010/0217399 A1 | 8/2010 | Groh |
| 2010/0274360 A1 | 10/2010 | Gunther |
| 2011/0029089 A1 | 2/2011 | Giuliani et al. |
| 2011/0106266 A1 | 5/2011 | Schwyzer et al. |
| 2011/0137424 A1 | 6/2011 | Lappin et al. |
| 2011/0144758 A1 | 6/2011 | Deffenbaugh |
| 2011/0276144 A1 | 11/2011 | Wirth et al. |
| 2011/0313533 A1 | 12/2011 | Gunther |
| 2012/0209392 A1 | 8/2012 | Angibuad et al. |
| 2012/0239156 A1 | 9/2012 | De Wilde et al. |
| 2013/0150972 A1 | 1/2013 | Iannotti et al. |
| 2013/0060346 A1 | 3/2013 | Collins |
| 2013/0090736 A1 | 4/2013 | Katrana et al. |
| 2013/0150974 A1 | 6/2013 | Iannotti et al. |
| 2013/0194353 A1 | 8/2013 | Hirai et al. |
| 2013/0197651 A1 | 8/2013 | McDaniel et al. |
| 2013/0261752 A1 | 10/2013 | Lappin et al. |
| 2014/0025173 A1 | 1/2014 | Cardon et al. |
| 2014/0107794 A1 | 4/2014 | Deffenbaugh et al. |
| 2014/0243986 A1* | 8/2014 | Frankle ............... A61F 2/4014 623/19.12 |
| 2014/0253641 A1 | 9/2014 | Furuya |
| 2014/0257499 A1 | 9/2014 | Winslow et al. |
| 2015/0223941 A1 | 8/2015 | Lang |
| 2015/0265411 A1 | 9/2015 | Deransart et al. |
| 2016/0045323 A1 | 2/2016 | Kovacs et al. |
| 2016/0270922 A1 | 9/2016 | Pressacco et al. |
| 2016/0302934 A1 | 10/2016 | Chavarria et al. |
| 2017/0056187 A1 | 3/2017 | Humphrey et al. |
| 2017/0071749 A1 | 3/2017 | Lappin et al. |
| 2017/0202674 A1 | 7/2017 | Gunther et al. |
| 2017/0209275 A1 | 7/2017 | Levy |
| 2017/0273806 A1 | 9/2017 | Cardon et al. |
| 2017/0304063 A1 | 10/2017 | Hatzidakis et al. |
| 2017/0360456 A1 | 12/2017 | Gunther |
| 2018/0071104 A1 | 3/2018 | Kovacs et al. |
| 2018/0078377 A1 | 3/2018 | Gargac et al. |
| 2018/0161169 A1 | 6/2018 | Cardon et al. |
| 2018/0193150 A1 | 7/2018 | Winslow et al. |
| 2018/0200067 A1 | 7/2018 | Axelso, Jr. et al. |
| 2018/0368982 A1 | 12/2018 | Ball |
| 2019/0336293 A1 | 11/2019 | Kehres |
| 2021/0038401 A1 | 2/2021 | Ball et al. |
| 2021/0137693 A1 | 5/2021 | Ball et al. |
| 2021/0236292 A1 | 8/2021 | Chavarria et al. |
| 2021/0244547 A1 | 8/2021 | Gunther et al. |
| 2021/0251640 A1 | 8/2021 | Gunther |
| 2022/0151795 A1 | 5/2022 | Running et al. |
| 2022/0175543 A1 | 6/2022 | Ball |
| 2022/0175544 A1 | 6/2022 | Ball et al. |
| 2023/0078024 A1 | 3/2023 | Gunther et al. |
| 2023/0080207 A1 | 3/2023 | Gunther et al. |
| 2023/0081505 A1 | 3/2023 | Gunther |
| 2023/0090753 A1 | 3/2023 | Running et al. |

FOREIGN PATENT DOCUMENTS

| | | |
|---|---|---|
| DE | 10164328 A1 | 7/2003 |
| EP | 0299889 A2 | 1/1989 |
| EP | 0339530 A2 | 11/1989 |
| EP | 0570816 A1 | 11/1993 |
| EP | 1464305 A1 | 10/2004 |
| EP | 1858453 | 11/2007 |
| EP | 1952788 A1 | 8/2008 |
| EP | 2601912 | 6/2013 |
| EP | 2083759 B1 | 9/2015 |
| EP | 3090705 | 11/2016 |
| FR | 2248820 A1 | 5/1975 |
| FR | 2567019 A1 | 1/1986 |
| FR | 2695313 A1 | 3/1994 |
| JP | 2013-158909 | 8/2013 |
| JP | 2014-515651 | 7/2014 |
| WO | WO 2006/093763 | 8/2006 |
| WO | WO 2008/011078 A2 | 1/2008 |
| WO | WO 2009/071940 A1 | 6/2009 |
| WO | WO 2011/112425 | 9/2011 |
| WO | WO 2013/148437 | 10/2013 |
| WO | WO 2012/075183 | 4/2014 |
| WO | WO 2014/067961 | 5/2014 |
| WO | WO 2014/195909 | 12/2014 |
| WO | WO 2017/184792 | 10/2017 |
| WO | WO 2018/022227 | 2/2018 |
| WO | WO 2018/129286 | 7/2018 |
| WO | WO 2018/181420 | 10/2018 |
| WO | WO 2019/178104 | 9/2019 |
| WO | WO 2019/213073 | 11/2019 |
| WO | WO 2020/185893 | 9/2020 |
| WO | WO 2023/183283 | 9/2023 |
| WO | WO 2024/026101 | 2/2024 |

OTHER PUBLICATIONS

U.S. Appl. No. 29/870,666, filed Feb. 1, 2023, Ball et al.

(56) References Cited

OTHER PUBLICATIONS

Biomet, "Absolute™ Bi-Polar." 2001 in 2 pages.
Biomet, "Copeland™ Humeral Resurfacing Head, Interlok®/HA Coated Implant Information," 2003 in 1 page.
Biomet, "Copeland™ Humeral Resurfacing Head," 2001 in 12 pages.
Biomet, "Copeland™ Humeral Resurfacing Head, Macrobond™ Implant Information," 2003 in 1 page.
Biomet, "Copeland™ Humeral Resurfacing Head, Surgical Technique," 2003 in 2 pages.
Boileau et al., "The Three-Dimensional Geometry of the Proximal Humerus. Implications for Surgical Technique and Prosthetic Design," J. Bone Joint Surg. Br. 79: 857-865, 1997.
Braun, et al., Modular Short-stem Prosthesis in Total Hip Arthroplasty: Implant Positioning and the Influence of Navigation, Ortho SuperSite (Oct. 2007) in 8 pages.
Clavert et al. Glenoid resurfacing: what are the limits to asymmetric reaming for posterior erosion? J. Shoulder and Elbow Surg. Nov./Dec. 2007: 843-848.
Dalla Pria, Paolo. Slide presentation, entitled "Shoulder Prosthesis Design and Evolution", to the Naples International Shoulder Congress in Italy (2000) in 55 pages.
DePuy, "Global C.A.P., Surgical Technique Resurfacing Humeral Head Implant," 2004 in 23 pages.
Inset Mini-glenoid Brochure, Titan Modular Shoulder System Brochure, Ascension Orthopedics, 2011, 4 pages.
Karduna et al. Glenhumeral Joint Translations before and after Total Shoulder Arthroplasty. J. Bone and Joint Surg. 79(8) (1997): 1166-1174.
Redacted letter from a third party dated Aug. 24, 2012 in 2 pages.
Levy et al., "Cementless Surface Replacement Arthroplasty of the Should. 5- to 10-year Results with the Copeland Mark-2 Prosthesis," J. Bone Joint Surg. Br. 83: 213-221, 2001.
Lima-Lto Medical Systems Glenoidi/Glenoids catalogue (2001) in 1 page.
Panisello, et al., Bone remodelling after total hip arthroplasty using an uncemented anatomic femoral stem: a three-year prospective study using bone densitometry, J Ortho Surg 14(1):32-37 (2006).
Ross, Mark and Duke, Phillip, "Early Experience In The Use of a New Glenoid Resurfacing Technique" Glenoid Presentation, SESA Nov. 4, 2006, Session 4/0800-0930 p. 93 in 1 page.
U.S. Appl. No. 29/683,368, filed Mar. 12, 2019, Ball et al.
Tight Fit Tools, Right Angle Drill Attachment, Serial No. 00400 www.tightfittools.com/riganat.html in 1 page/downloaded Mar. 11, 2005.
Titan(™) Modular Shoulder System Brochure, 2011, available at http://www.ascensionortho.com/Assets/PDF/TitanModular/TITANModularShoulder_Brochure-revD.pdf (2 pages).
Tournier et al., Enhancement of Glenoid Prosthesis Anchorage using Burying Technique. Techniques in Shoulder & Elbow Surgery 9(1)(2008):35-42.
Wang et al., Biomechanical Evaluation of a Novel Glenoid Design in Total Shoulder Arthroplasty. J. Shoulder & Elbow Surgery (2005) 15: 129S-140S.
Lima-Lto Miniglenoide Cementata document 7560.50.030 (1999) in 1 page.
Statement of Grounds and Particulars of Opposition for Australian Patent Application No. 2006218936 dated Oct. 5, 2012 in 8 pages.
U.S. Appl. No. 18/349,805, filed Jul. 10, 2023, Gunther.
U.S. Appl. No. 18/477,416, filed Sep. 28, 2023, Running et al.

\* cited by examiner

TOTAL SHOULDER PROSTHESIS HAVING INSET GLENOID IMPLANT CONVERTIBLE FROM ANATOMIC TO REVERSE

This application is a continuation of U.S. Ser. No. 15/952,063, filed Apr. 12, 2018, now U.S. Pat. No. 11,065,125, which claims the benefit of priority from U.S. Provisional No. 62/485,839, filed Apr. 14, 2017, which are hereby incorporated by reference in their entireties.

BACKGROUND

Shoulder Replacement is a commonly performed medical procedure for treatment of osteoarthritis, rheumatoid arthritis, as well as for treatment of certain deformities related to oncological indications as well as trauma. There are two primary types of articulations available to surgeons for treatment: anatomic and reverse. With anatomic, the surgeon replaces the articular surfaces with industrial materials such that the articulating surfaces are substantially the same shape as the natural anatomy. A stem can be commonly fixed inside the canal of the humerus, a metallic articular head can be rigidly fixed to the proximal aspect of the same, the articular head having a convex articular surface adapted to articulate with the glenoid implant. The glenoid implant can include on its back side (medial side) certain pegs or posts or fins adapted to be rigidly fixed within the glenoid fossa of the scapula and on its front side a concave or flat articular surface adapted to articulate with the humeral head of the humeral implant.

When a reverse prosthesis is used, the articular surface is reversed in that the metallic ball is rigidly fixed to the glenoid fossa of the scapula, and the concave articular surface is rigidly fixed to the humeral bone, thereby reversing the fashion of articulation of the prosthesis.

The surgeon chooses between the two types of prostheses by assessing a number of conditions of the patient including level of pain, patient activity level, deformity or severity of the boney degradation, the strength of surrounding soft tissues, and present or absence of prior surgery, and particularly the health and strength of the rotator cuff muscle and tendon. Disease of the rotator cuff is common among patients with arthritis of the shoulder. In this circumstance, it is commonly observed that the absence of insufficiency of the rotator cuff leads to a condition where the anatomic shoulder replacement prosthesis is not sufficiently stabilized by surrounding soft tissue. In this case, a reverse shoulder replacement prosthesis can be preferred in some cases due to the higher inherent stability of the articulation. In addition, the reverse prosthesis can advantageously utilize the remaining muscles in a way they can be more effective in the absence of the other soft tissue structures by adjusting the position of the articular surfaces within the joint.

It is not uncommon that a surgeon selects to use an anatomic prosthesis and is provides effective treatment to the patient though the shoulder replacement operation. However, over time and during use of the prosthesis, the patient's rotator cuff complex can become insufficient, tear, or generally be diseased such that it can no longer perform its function associated with normal joint kinematics. In this case, the surgeon can elect to perform a second operation to remove the anatomic prosthesis, and replace the anatomic prosthesis with a reverse prosthesis.

Several attempts have been made to attempt to address the need of conversion of the articular surface without interruption of the fixation. Primarily, these are created using a two (or more) system, where there is a metallic fixation component which is rigidly fixed to the glenoid fossa, and a polyethylene (PE) articular component which is secondarily fixed to the metallic component, and provides the concave articular surface adapted to articular with the humeral prosthesis. While referred to herein as a PE component, some embodiments do not require the use of polyethylene and can be made of other biocompatible materials depending on the desired clinical result. The PE component is commonly fixed to the metallic fixation component by conventional industrial techniques such as snap fit mechanisms, snap rings, compression pins, overmolding of the PE and other such means.

A challenge of this particular articulation in some cases is that the glenoid fossa is relatively small, and commonly there is much reduced presence of bone in patients with arthritis. In this context, the surgeon has limited positioning and bone to work with in order to fit within the patient. In addition, the surgeon must be careful not to overstuff the joint, meaning implant components that move the new articulating surface far from its original position such that the soft tissues is unnaturally tensioned, which can lead to instability, accelerated where, soft tissue failure, pain, reduced range of motion, or fracture of the prosthesis and surrounding bone. Facing these conditions, the prosthesis typically needs to be designed to remain relatively thin (commonly, 1 piece, where PE glenoid implants typically have a 4 mm thick articular surface). In order to design these modular components, there can be little additional packaging space provided into which to fit the attachment mechanisms necessary for use without adversely affecting the performance of the overall joint replacement procedure. Thus, typically, these designs lead to "over-optimization" of the fixation and articular portions in order to provide sufficient attachment mechanisms such that either: the PE is too thin to be sufficiently strong, the metallic components are too small to provide sufficient fixation, or the overall mechanism is insufficiently rigid causing there to be secondary wear surfaces, and generation of wear particles leading to PE disease.

A problem that can exist is that in the case where the surgeon wants to change the prosthesis type, the anatomic prosthesis is commonly well fixed and adapted to the patient's body such that removal of the prosthesis can be very destructive, and leave natural bone remaining that is perhaps insufficient to support the fixation of the reverse prosthesis. What is needed is a prosthesis system that provides a means by which the articulating surfaces of the implant can be exchanged such that the anatomic surfaces can be converted to reverse surfaces, while not exchanging the fixation components.

What is also needed is a simple means by which the surgeon can implant an inset anatomic articulating glenoid implant whereby at a later date, can remove the anatomic articulating surface and replace it with a reverse articulating surface such that the primary means of fixation remains well fixed in the glenoid fossa at the moment of articular exchange.

SUMMARY

In some embodiments, disclosed herein is a method of performing a reversible anatomic shoulder replacement procedure. The method can include any number of: reaming a cavity into the glenoid; and inserting an anatomic glenoid articular implant into the glenoid cavity, the glenoid anatomic articular implant comprising a medial surface configured to mate with the glenoid cavity, a central peg extending medially from the medial surface, a lateral surface configured to articulate with a humeral component; and an intermediate component between the lateral surface and the medial surface, the intermediate component having an outer diameter reversibly attached to a snap ring attached to a fixation ring, the snap ring and the fixation ring at least partially implanted within the glenoid cavity. The anatomic glenoid articular implant can be partially or fully inset into the glenoid cavity. The cavity could be circular, oval, or another shape.

Also disclosed herein is a method of converting an anatomic to a reverse shoulder prosthesis, including any number of: identifying a patient with an anatomic glenoid articular implant within a glenoid cavity, the anatomic articular implant comprising a medial surface mated with the glenoid cavity, a central peg extending medially from the medial surface, a lateral surface articulating with a humeral component; and a central component between the lateral surface and the medial surface, the central component having an outer diameter reversibly attached to a snap ring and a fixation ring, the snap ring and the fixation ring at least partially implanted within the glenoid cavity; inserting a implant removal tool through the lateral articulating surface of the anatomic glenoid articular implant sufficient to collapse the snap ring; removing the anatomic glenoid articular implant while leaving the fixation ring in place within the glenoid cavity; and inserting a reverse shoulder implant into the glenoid cavity sufficient to actuate the snap ring such that the reverse shoulder implanted is reversibly fixed to the fixation ring. Inserting the removal tool can include driving pins, a drill bit, or another tool of the removal tool through the lateral articulating surface of the anatomic glenoid articular implant.

In some embodiments, also disclosed herein is a reversible anatomic shoulder replacement system, that can include any number of: a fixation ring configured to be positioned within the glenoid cavity, the fixation ring comprising a peripheral edge comprising an outer diameter and a plurality of spaced-apart radially inward indents in the peripheral edge, the fixation ring comprising a groove configured to house a snap ring therein; a snap ring comprising an expanded configuration and a collapsed configuration; and an anatomic articular implant comprising a medial surface configured to mate with the glenoid cavity, a central peg extending medially from the medial surface, a lateral surface configured to articulate with a humeral component; and an intermediate component between the lateral surface and the medial surface, the intermediate component having an outer diameter reversibly attached to the snap ring and the fixation ring, the snap ring and the fixation ring configured to be at least partially implanted within the glenoid cavity. The groove can include anti-rotation tabs. The peripheral edge of the fixation ring can be configured to facilitate bone ingrowth, e.g., via an osteoinductive or osteoconductive surface. The groove can be a circumferential groove. The lateral surface can include any appropriate material, such as polyethylene.

Also disclosed herein is a reverse shoulder replacement kit for an anatomic shoulder replacement system, that can include any number of: an implant removal tool configured to bore through a medial surface of the anatomic glenoid articular implant sufficient to collapse a snap ring; and remove an anatomic glenoid articular implant while leaving a fixation ring in place within the glenoid cavity; and a reverse shoulder implant configured to be implanted into the glenoid cavity, the reverse shoulder implant comprising a generally cylindrical component comprising a medial surface configured to mate with the glenoid cavity, a central receptacle for housing an articular post therethrough, and a plurality of peripheral screw holes; a lateral surface, and a central post extending away from the lateral surface, wherein the reverse shoulder implant is configured to reversibly mate with the snap ring and fixation ring embedded in the glenoid cavity to anchor the reverse shoulder implant.

DETAILED DESCRIPTION

Figure 1:
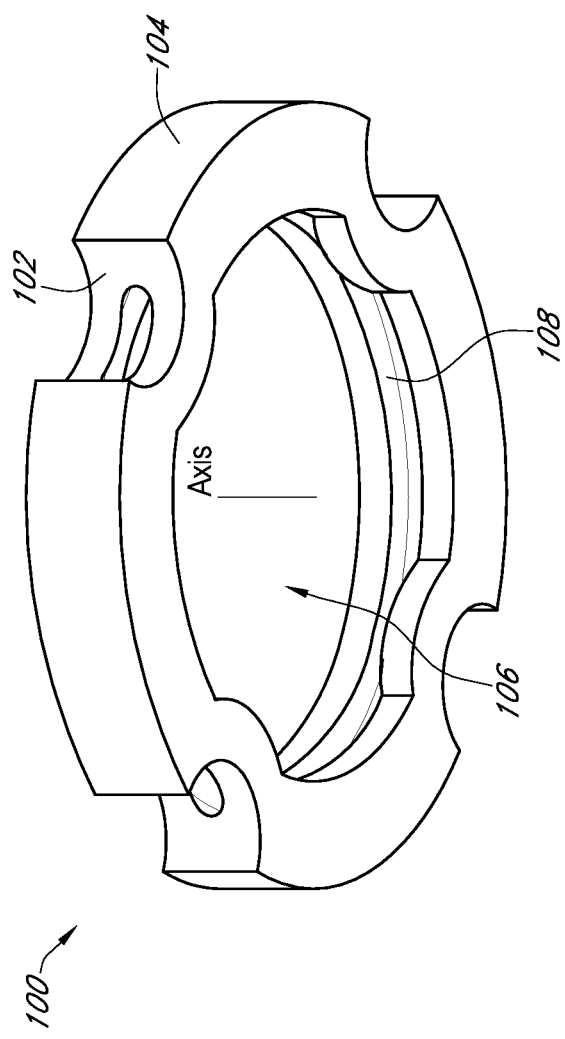
FIG. 1 illustrates a lower perspective view of an embodiment of a fixation support which can be an annular fixation ring in some embodiments that can be fixed at least partially within a prepared glenoid cavity.

In particular, some embodiments of the invention are focused on advantageously exchanging the articular surface of the glenoid from a concave shape to a convex shape, without removing the components or interface having to do with fixation of the implant into the glenoid fossa.

In some embodiments, embodiments of the invention can be used or modified with use with particular advantages of using inset glenoid fixation technology in anatomic shoulder arthroplasty, such as described, for example, in U.S. Pat. Nos. 8,007,538 and/or 8,778,028 to Gunther, which are hereby incorporated by reference in their entireties.

What is further described are methods by which the surgeon can achieve the use of the inset glenoid technology with an anatomic articulation, while after having the ability to convert the technology to a reverse articulation, without requiring removal the rigid fixation between the inset fixation and the scapula bone (in other words, allowing the rigid fixation support between the inset fixation and the scapula bone to remain in place during conversion from an anatomic to a reverse prosthesis).

Some embodiments of the invention can utilize an inset glenoid articulation implant described by Gunther et al. including in U.S. Pat. No. 8,007,538 or U.S. Pat. No. 8,778,028. However, some embodiments of the invention can also utilize onlay glenoid articulation implants. The peripheral rim of the implant can in some cases have an important role in the fixation stability of the implant and its resistance to motion relative to the glenoid bone during articulation. In addition, it is recognized that a known "rule of thumb" in the industry is that the bearing component of the glenoid implant, such as the polyethylene (PE) component, should be at least about 3 mm thick at its thinnest position in order to achieve a sufficient material strength to minimize risk of accelerated implant failure. Of course, this rule is only a guide, but has proven helpful in assessing longevity of implant designs. With these points in mind, it is recognized that in some embodiments the design of the implant (which can be inset in some embodiments) might be improved upon by providing a step in the outer diameter of the inset glenoid implant at its most medial aspect while being able to maintain a minimum PE thickness of about or at least about 2 mm, 2.5 mm, 3 mm, 3.5 mm, 4 mm, or ranges incorporating any of the aforementioned values. In the space that this step provides is placement of an annular ring which can be rigidly fixed on the outer diameter of the articular implant such that the outer diameter of the inset glenoid implant remains a contiguous surface, albeit in some embodiments made a plurality of materials: the lateral aspect being part of the PE articulation, the medial aspect being the outer diameter of the annular ring, which can be metallic in some cases. The annular ring and the PE articular component can be attached to one another through the use of a snap ring mechanism or other ways, some of which are described elsewhere herein.

The annular ring can be configured such that its outer diameter presents a surface to the surrounding bone which can be adapted to be biologically attractive for the growth of surrounding bone tissue. This technology can be achieved by several means such as, for example, various coatings or secondary manufacturing operations, mechanical modification through machining operations, creation of an adapted surface using 3D printing manufacturing, or other means. One advantage of the surface on the outer diameter is such that over the course of the healing process following surgery, bone grows and adapts itself to this annular ring so as to provide rigid attachment of surrounding bone to the annular ring. Thus, at the moment of articular component exchange, the ring is well fixed to bone, and following removal of the PE articulation component, the ring remains well fixed within the glenoid bone, and can be useful as a support surface in attachment of a new reverse articulating surface to the bone.

FIG. 1 illustrates a lower perspective view of an embodiment of a fixation support which can be an annular fixation ring in some embodiments that can be fixed at least partially within a prepared glenoid cavity. The annular ring 100 can include a central cavity 106 and a plurality of radially inward indents 102 in the outer circumference of the peripheral edge 104 of the annular ring 100 as shown and be sized and configured for fixation screw clearance. The ring 100 could have any number of indents 102 such as 1, 2, 3, 4, 5, 6, 7, 8, 9, 10, or more, or ranges including at least two of the aforementioned values. The indents 102 could be regularly or irregularly spaced apart along the circumference in some embodiments, and have a curved shape as shown or other shapes. As shown, the peripheral edge 104 can include a coating or other surface, e.g., osteoinductive or osteoconductive surface to facilitate bone ingrowth and fixation into the cavity. The surface could include, for example, cortical bone, cancellous bone, particulate matter, a powder form, granules, chips, a synthetic bone substitute, growth factors and/or bone growth promoting proteins, or combinations thereof. The annular ring 100 can also include a groove or slot 108 that can be oriented along the outer circumference of the central cavity 106 (e.g., inner diameter of the ring) and configured to house a snap ring therein (not shown).

Figure 2:
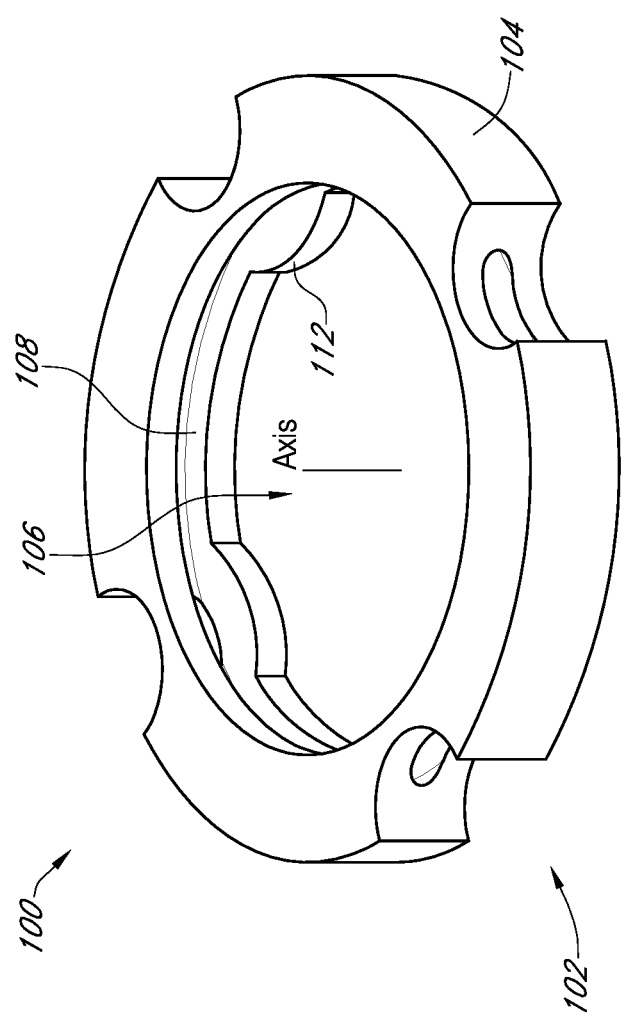
FIG. 2 illustrates an upper perspective view of an embodiment of a support, e.g., an annular ring 100.

FIG. 2 illustrates an upper perspective view of an embodiment of a support, e.g., an annular ring 100, showing the indents 102 as previously described. Also shown is the groove or slot 108 configured to house a snap ring as well as radially-inward extending anti-rotation tabs 112. The outer diameter of the peripheral edge 104 of the annular ring 100 can match that of a bearing, e.g., polyethylene component in some embodiments.

Figure 3:
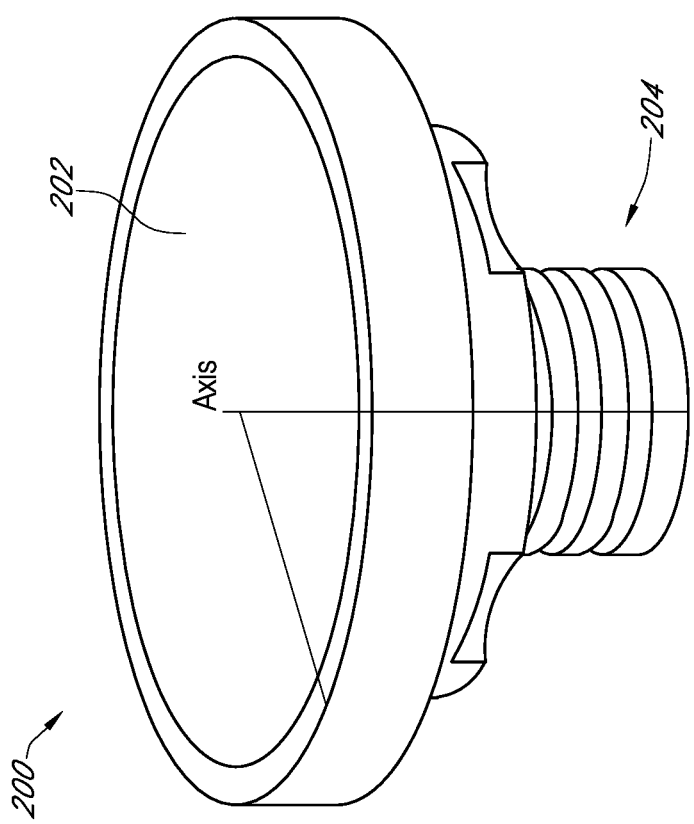
FIGS. 3 and 4 illustrate an embodiment of an anatomic articular component 200 for a glenoid cavity which can be made of polyethylene or another appropriate material.
Figure 4:
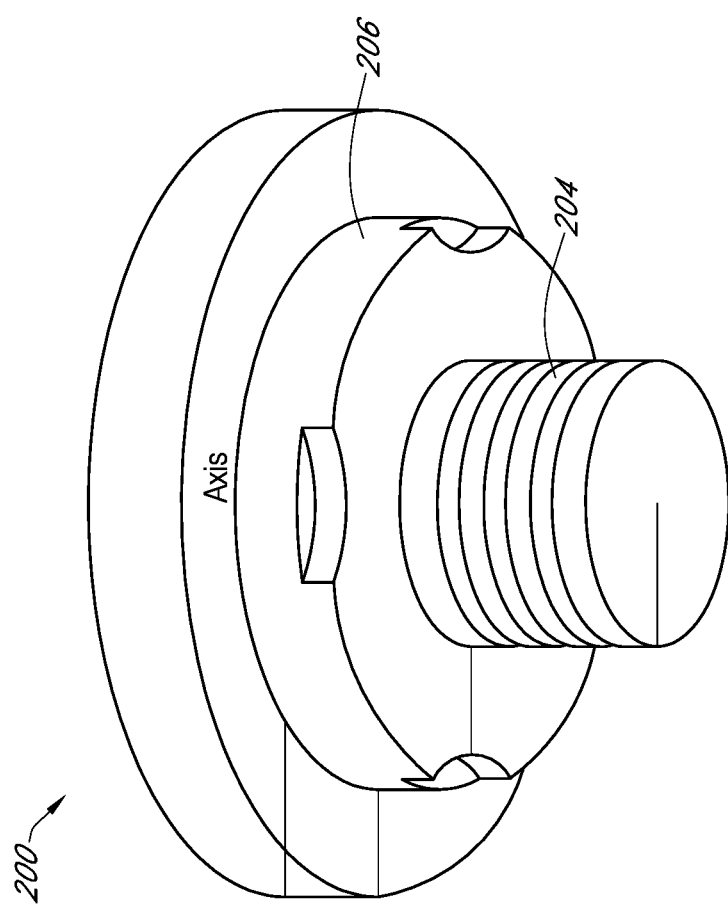

FIGS. 3 and 4 illustrate an embodiment of an anatomic articular component 200 for a glenoid cavity which can be made of polyethylene or another appropriate material. The anatomic articular component 200 can include a concave articulating surface 202 as shown, as well as a central fixation post or peg 204, which can be only a single post or peg in some cases, and be aligned coaxially with the center of the implant. The peripheral edge of the implant could have a generally cylindrical shape in some embodiments, and/or have a circular, oval, or other cross-section. The articular component 200 can also include a feature configured to mate with the fixation support, such as a cylindrical component 206 lateral to the articular surface 202 that can have an outer diameter that corresponds to the inner diameter of the fixation support (not shown) as well as a slot or groove (not shown) configured to house a snap ring (not shown). The outer diameter of the component 206 can be in some cases less than, such as about or at least about 5%, 10%, 20%, 30%, 40%, 50%, or more less than that of the outer diameter of the articulating surface 202 of the anatomic articular component 200, or ranges including any two of the aforementioned values.

Figure 5:
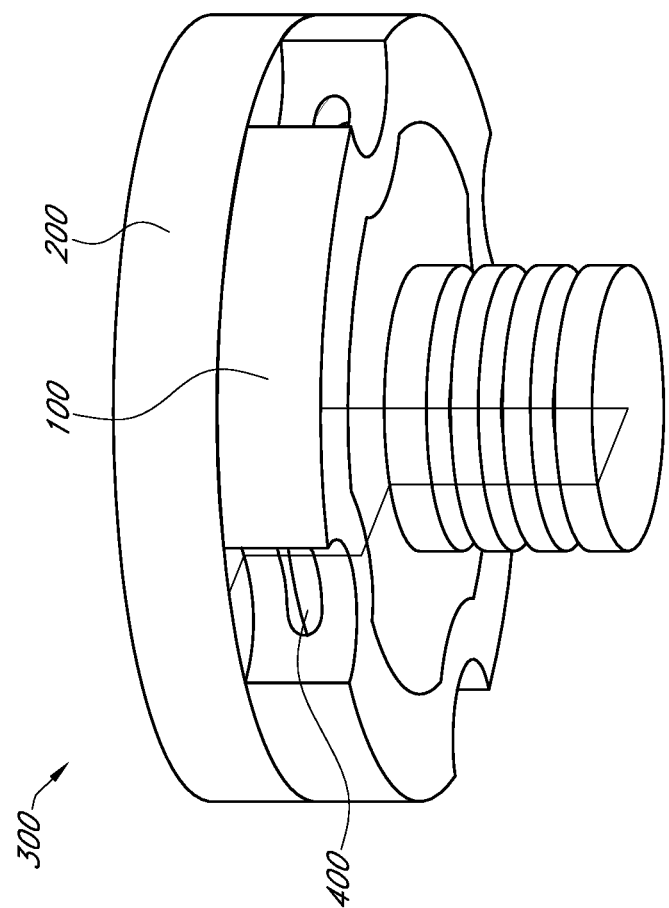
FIGS. 5 and 6 illustrate different perspective views of an embodiment of a reversible anatomic articular assembly 300 including the anatomic articular component 200, fixation ring 100, and location for placement of a snap ring 400.
Figure 6:
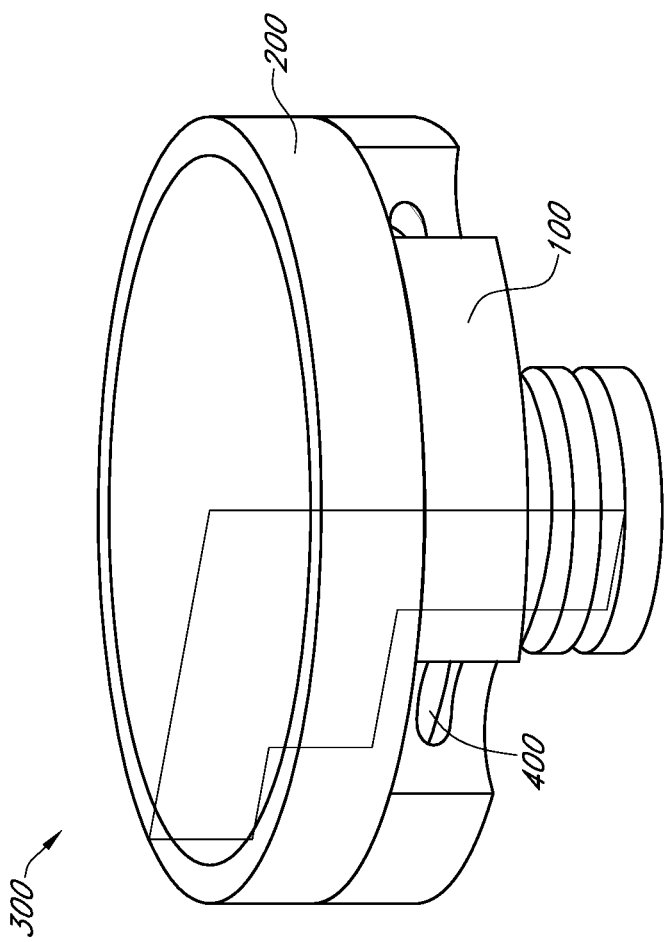

FIGS. 5 and 6 illustrate different perspective views of an embodiment of a reversible anatomic articular assembly 300 including the anatomic articular component 200, fixation ring 100, and location for placement of a snap ring 400 as previously described and illustrated.

Figure 7:
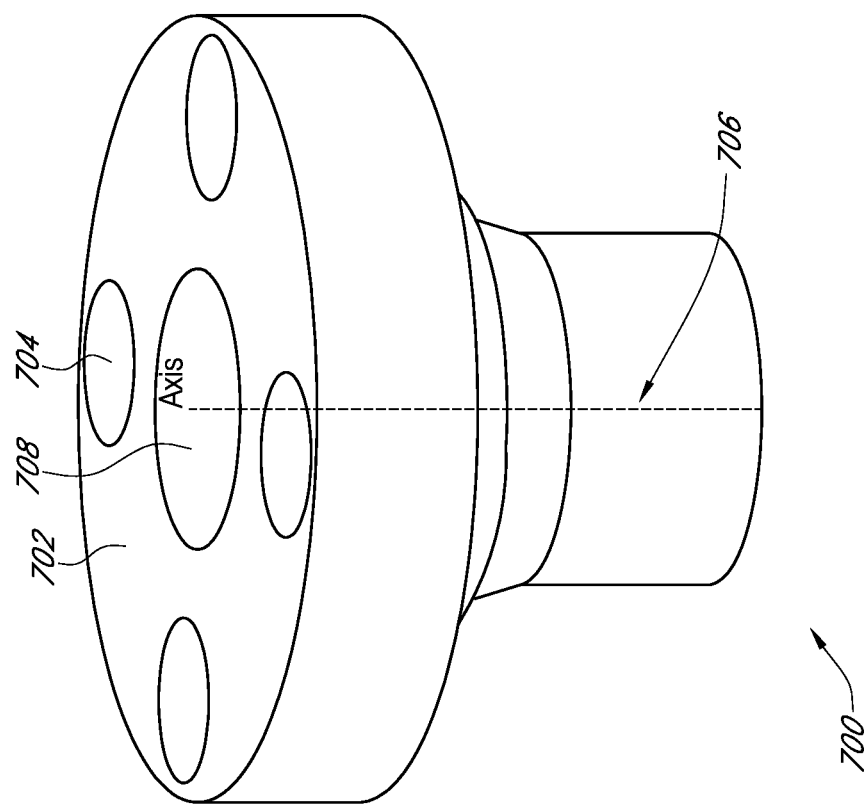
FIG. 7 illustrates a perspective view of an embodiment of a reverse fixation disc 700 including a central fixation post 706 that can include a longitudinal axis aligned along the center of the reverse fixation disc as shown.

FIG. 7 illustrates a perspective view of an embodiment of a reverse fixation implant, e.g., disc 700 including a central fixation post 706 that can include a longitudinal axis aligned along the center of the reverse fixation disc as shown. The medial surface 702 of the disc can include a central receptacle 708 for an articular post, as well as a plurality, e.g., 2, 3, 4, or more screw holes 704 oriented more peripherally with respect to the peripheral edge 706 of the disc, which can be generally cylindrical as shown, or another suitable geometry.

Figure 8:
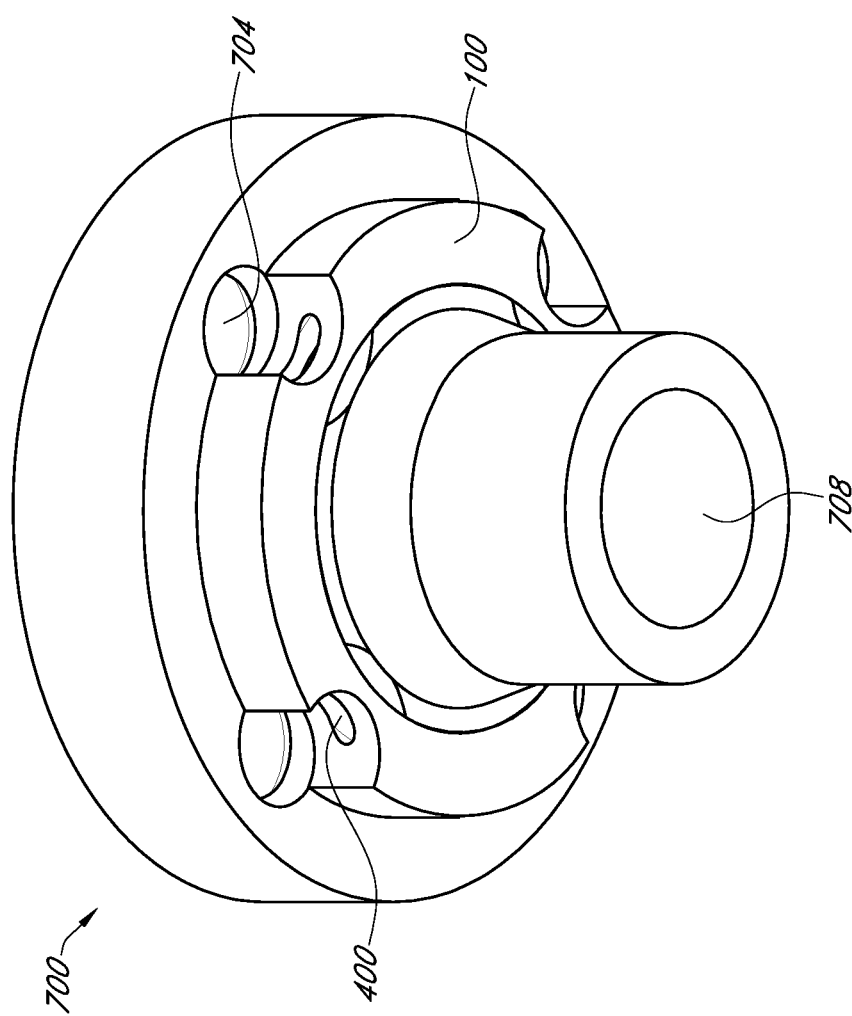
FIGS. 8 and 9 illustrate perspective views of a reverse fixation disc 700 including peripheral screw holes 704, fixation ring 100 and snap ring 400, the snap ring 400 which can have the same mechanism as the anatomic assembly described herein.
Figure 9:
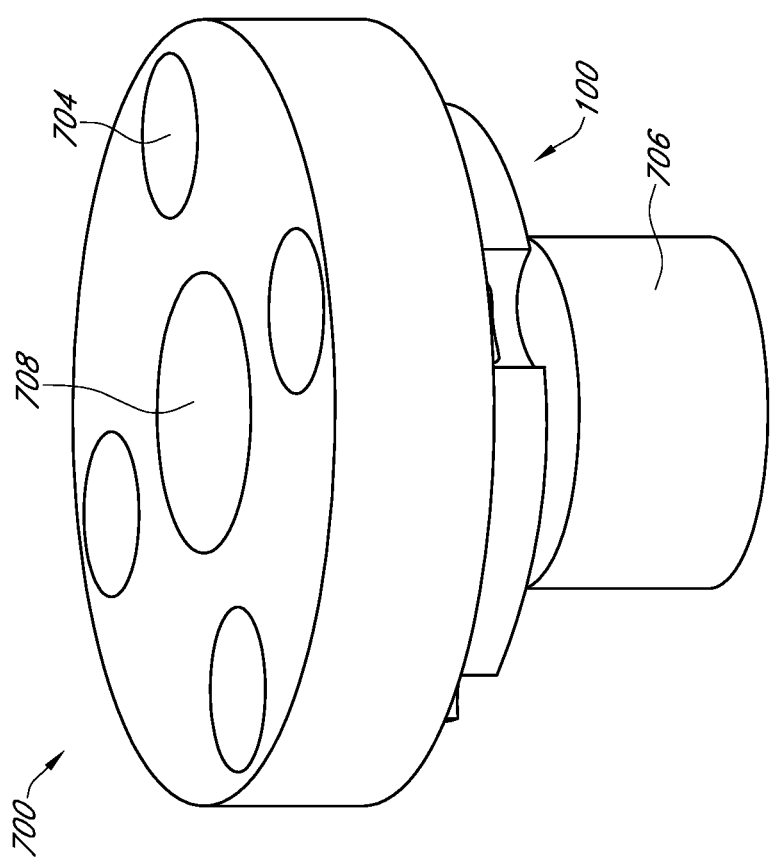

FIGS. 8 and 9 illustrate perspective views of a reverse fixation disc 700 including peripheral screw holes 704, fixation ring 100 and snap ring 400, the snap ring 400 which can have the same mechanism as the anatomic assembly described herein. Also shown is the other end of the receptacle 708 for the articular post that can extend through the implant. The apertures 704 (e.g., screw holes) can be axially aligned and configured to correspond with each of the indents 102 of the fixation ring 100 with the indents 102 as previously described, to house fixation screws therethrough.

Figure 10A:
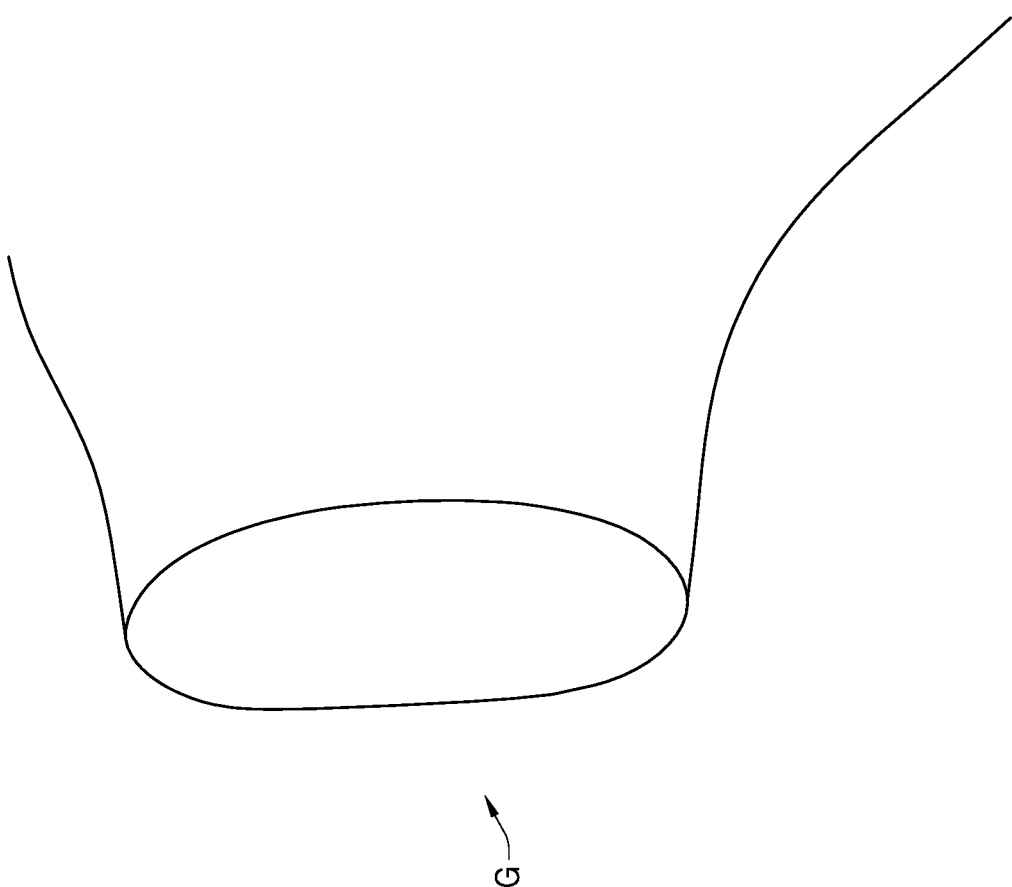
FIGS. 10A-C illustrate part of a method of implanting an anatomic prosthesis into a reamed glenoid cavity, according to some embodiments of the invention.
Figure 10B:
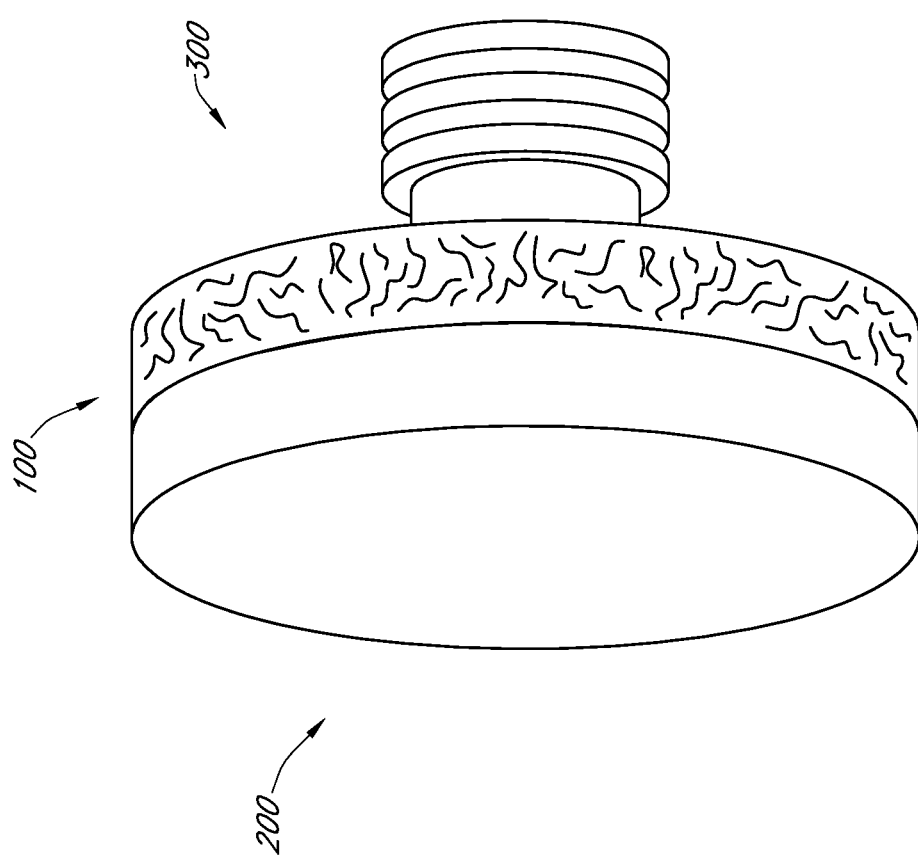
Figure 10C:
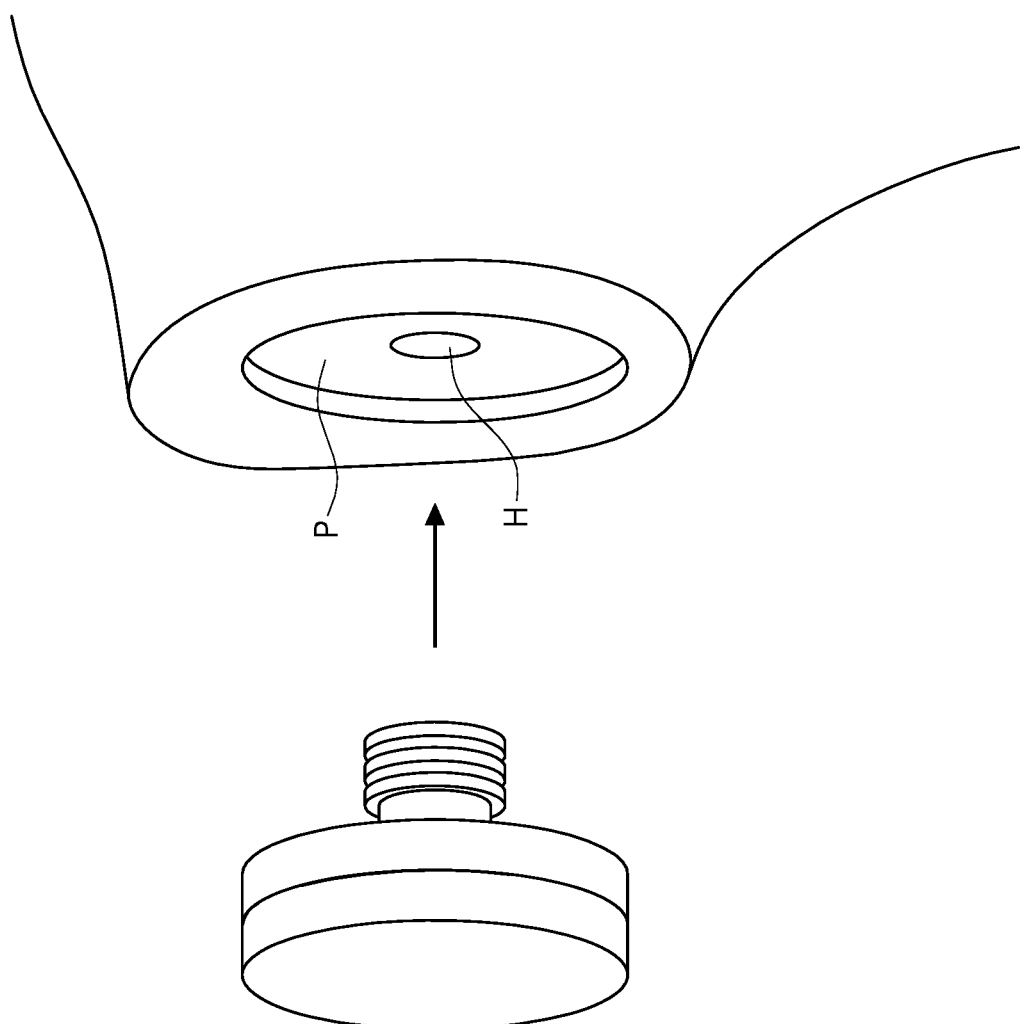

FIGS. 10A-10C illustrates part of a method of implanting an anatomic prosthesis into a reamed glenoid cavity, according to some embodiments of the invention. A pocket P can be prepared, such as by reaming, in the glenoid G (shown in FIG. 10A), which can be an appropriate shape, such as circular as shown, ovoid, or other geometries, with a central distal extending hole H for a central peg in some embodiments, as shown in FIG. 10C. The anatomic implant, one embodiment of which is shown in FIG. 10B along with the fixation ring and snap ring, can be implanted into the cavity, shown schematically in FIG. 10C such as in a partially or completely inset manner, with about or at least about 10%, 20%, 30%, 40%, 50%, 60%, 70%, 80%, 90%, or 100% of the thickness of the peripheral edge of the implant inset below the prepared glenoid surface, or ranges including any two of the aforementioned values. The attachment of the ring to the PE implant can be preferably achieved in a reversible fashion using techniques and tools available to a surgeon such that the operation can be performed in situ, or in place within the patient. In order to accomplish this, a snap ring mechanism can be utilized such that another component, such as an angular metallic ring is positioned between the bearing component, e.g., PE component and the snap ring and/or metallic ring.

Figure 11A:
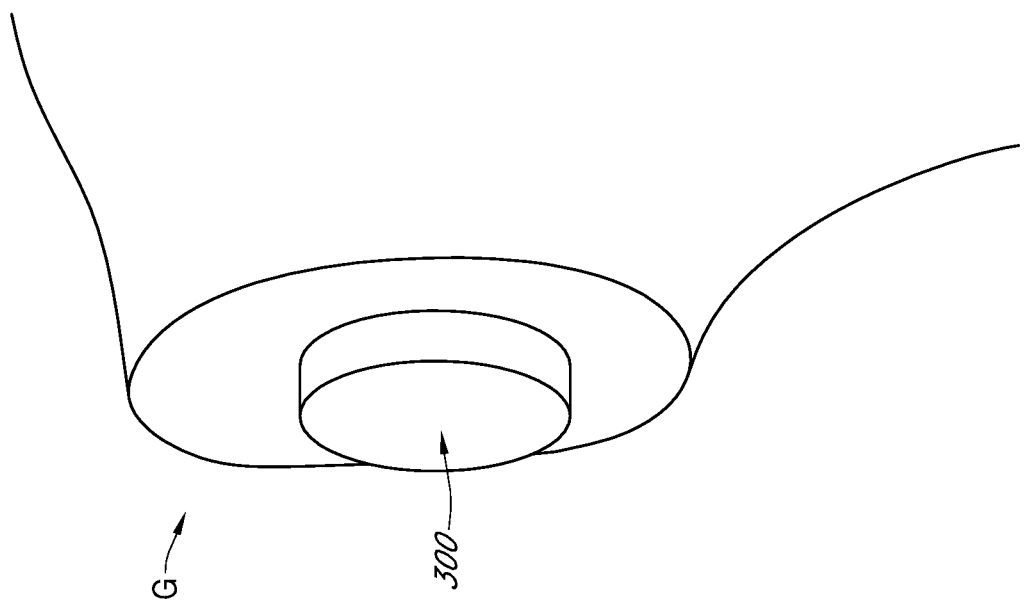
FIGS. 11A-D and 12A-B illustrate a method of removing an anatomic prosthesis while leaving a fixation ring in place embedded in the glenoid cavity, as well as embodiments of components for use in the method, according to some embodiments.
Figure 11B:
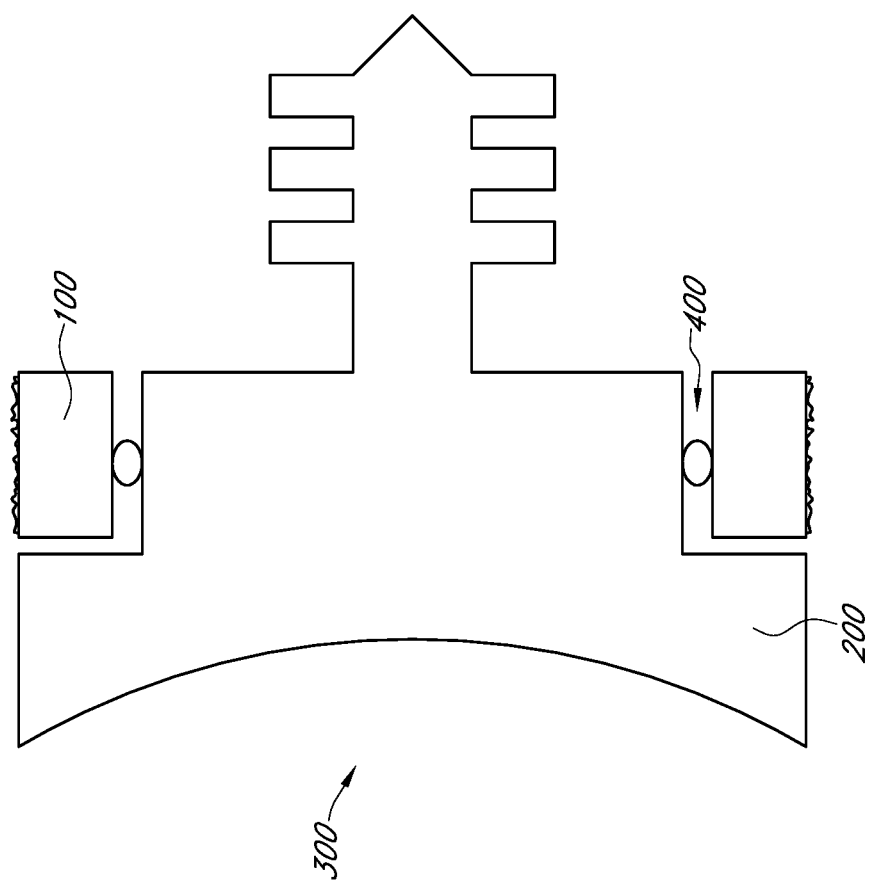
Figure 11C:
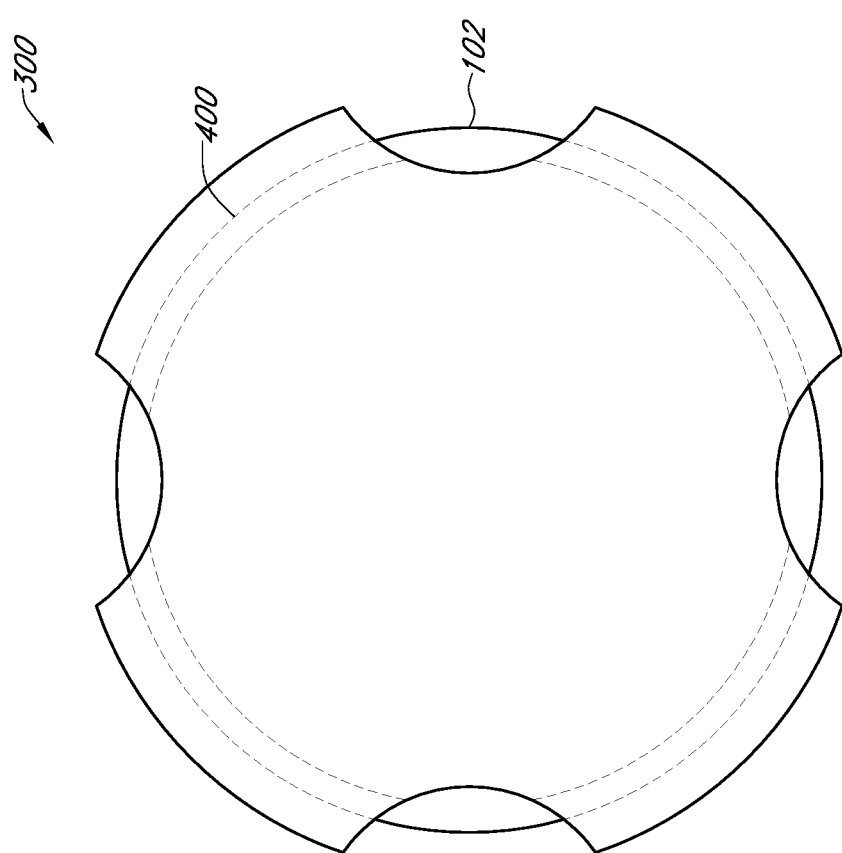
Figure 11D:
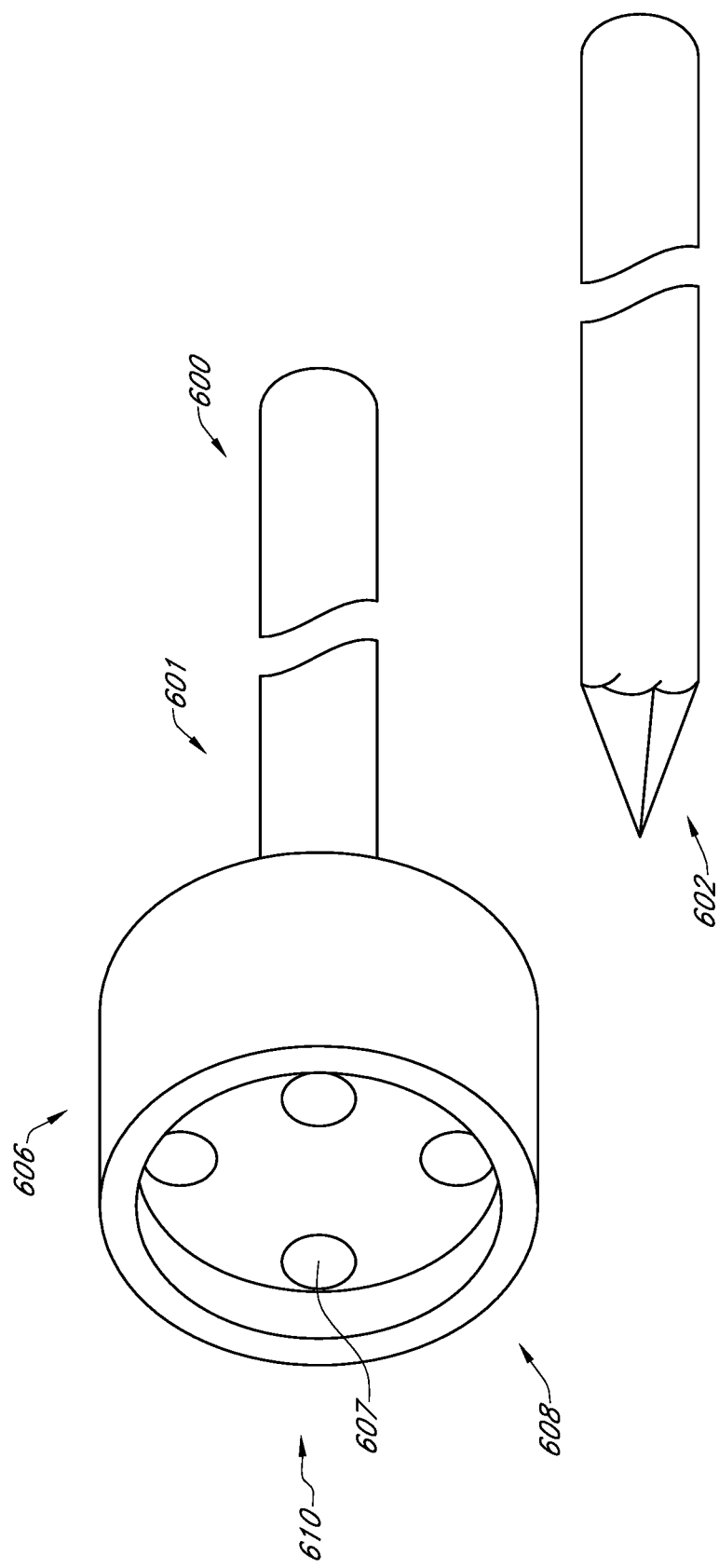

FIG. 11A schematically illustrates an anatomic articular implant 300 inserted into bone, such as the glenoid cavity. FIG. 11B schematically illustrates a side view, and FIG. 11C a top view, of an implant that can be as previously described. As shown in FIGS. 11A-D and 12 in some embodiments, at the moment the surgeon seeks to remove the PE component from the annular ring, the snap ring 400 (shown in phantom in FIG. 11C) can be collapsed in order to eliminate its interference fit between the annular ring and the PE component. This can be performed through the use of a guide 600 shown in FIG. 11D which can be placed over the surface of the PE component which can be in situ. In some embodiments, the guide 600 can have an elongate shaft 601 and a distal end 604 including an annular sidewall 606 defining a cavity 608 and an open distal end configured to have an inner diameter that can match, substantially match, or be the same size or larger than the outer diameter of the peripheral edge of the bearing component of the implant, such that the annular sidewall 606 and cavity 608 is placed over the glenoid implant. Release pins 602, a drill, or other tool can be axially advanced into apertures 607 of the guide 600 to facilitate release of the snap ring from the glenoid implant.

Figure 12A:
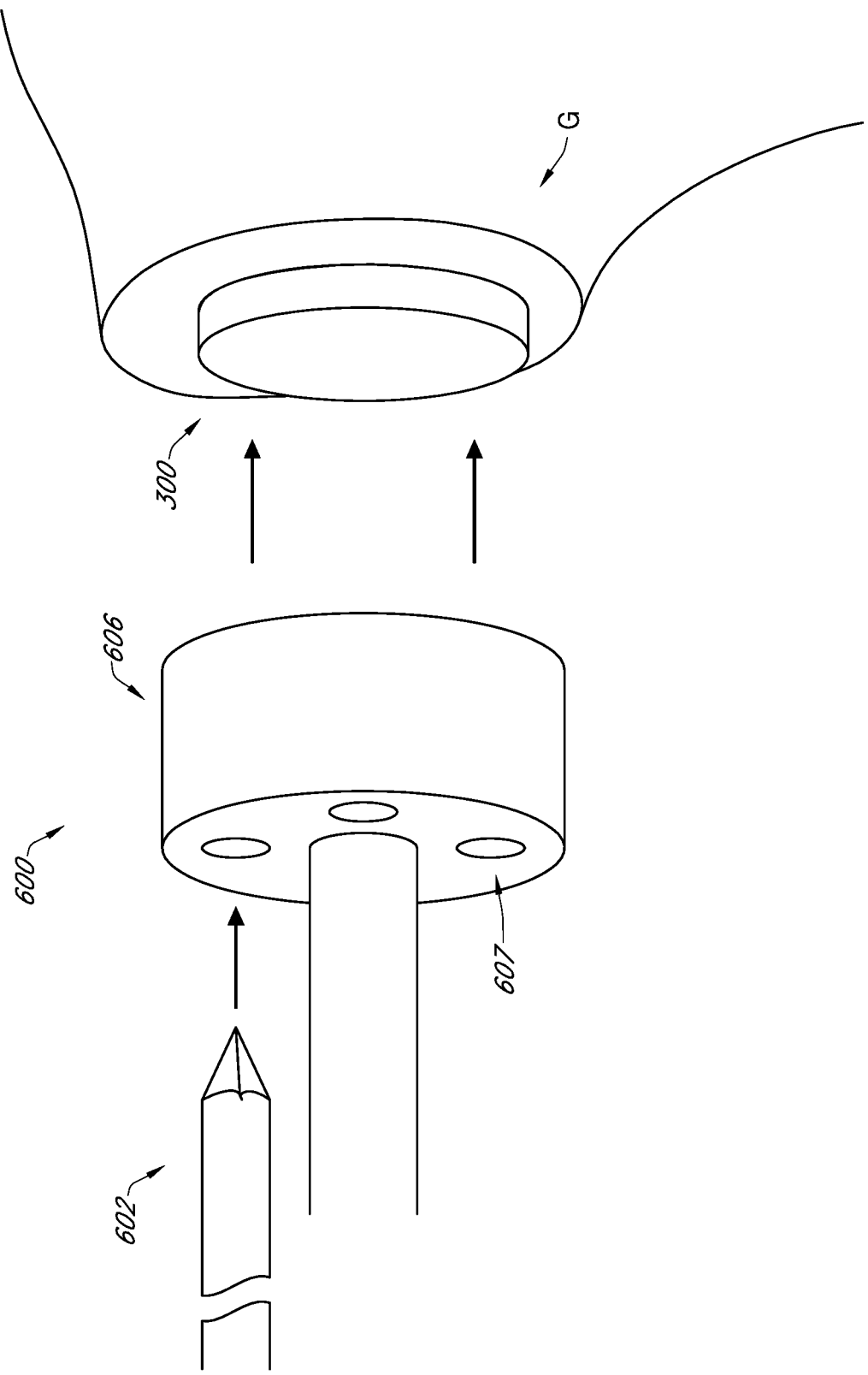
Figure 12B:
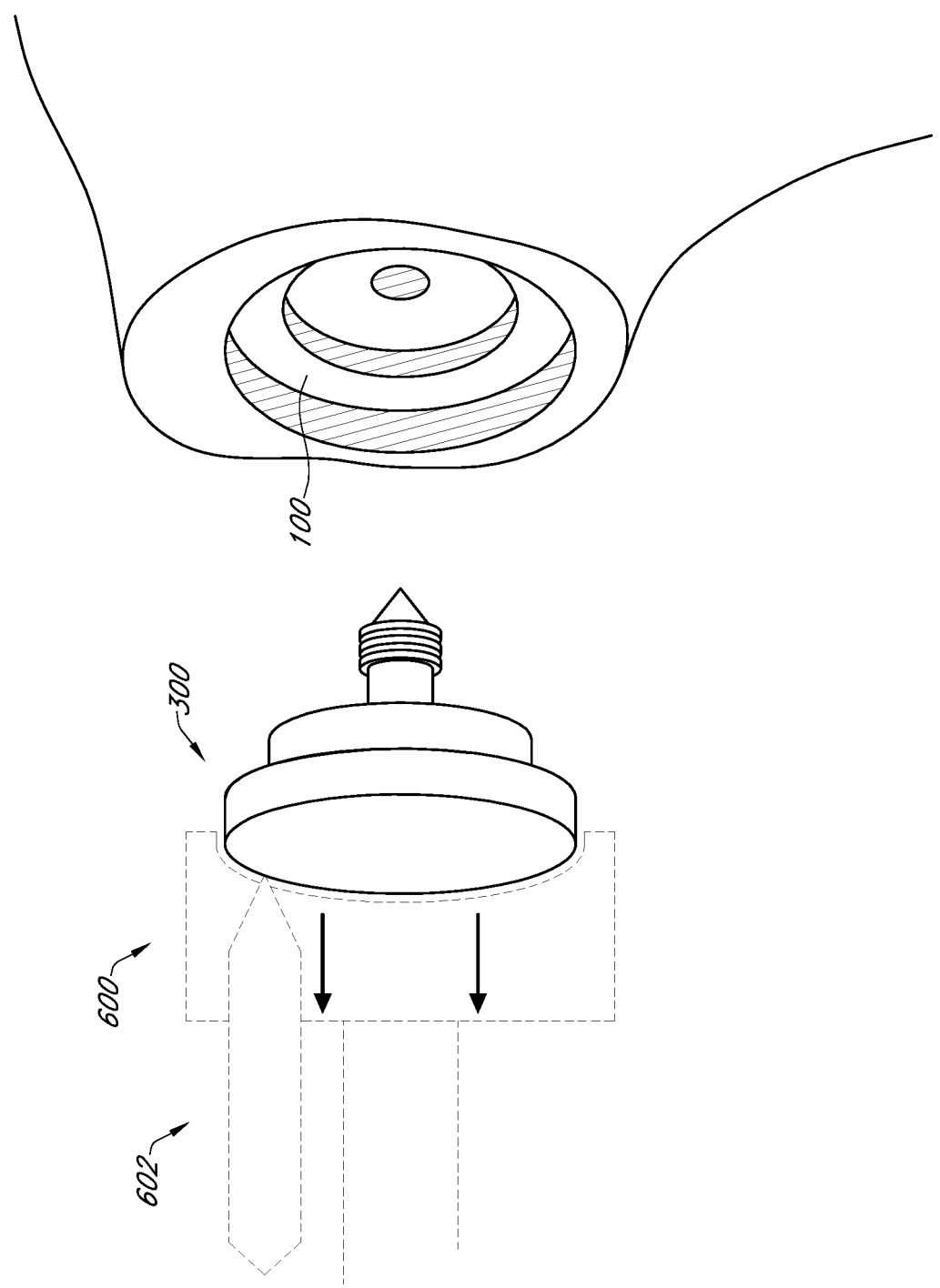

The guide 600 provides positioning of a plurality of holes, e.g., about or at least about two, three, four, five, or more holes positioning around the periphery of the PE implanted such that which a drill or pin 602 is mechanically driven into the guide holes 607, they are aligned to force the snap ring 400 in an radially inward fashion to allow for release of the snap ring. FIG. 12A schematically illustrates the guide 600 being advanced toward the glenoid implant 300 in situ in the glenoid G, along with pins 602 that can be placed in apertures 607 of the guide 600. Once a number of pins 602, e.g., three pins are driven through the guide and PE component, the snap ring is collapsed, and the PE component and snap ring can be removed from the annular fixation ring as an assembly, as shown in FIG. 12B. At this point, what remains is the annular fixation ring well fixed within the glenoid fossa. In some embodiments, the fixation ring may not be fully counter-sunk, and be partially rather than fully inset, within the glenoid surface, and/or stand proud of the glenoid surface. With time, the fixation ring can have some bony ingrowth.

Figure 13A:
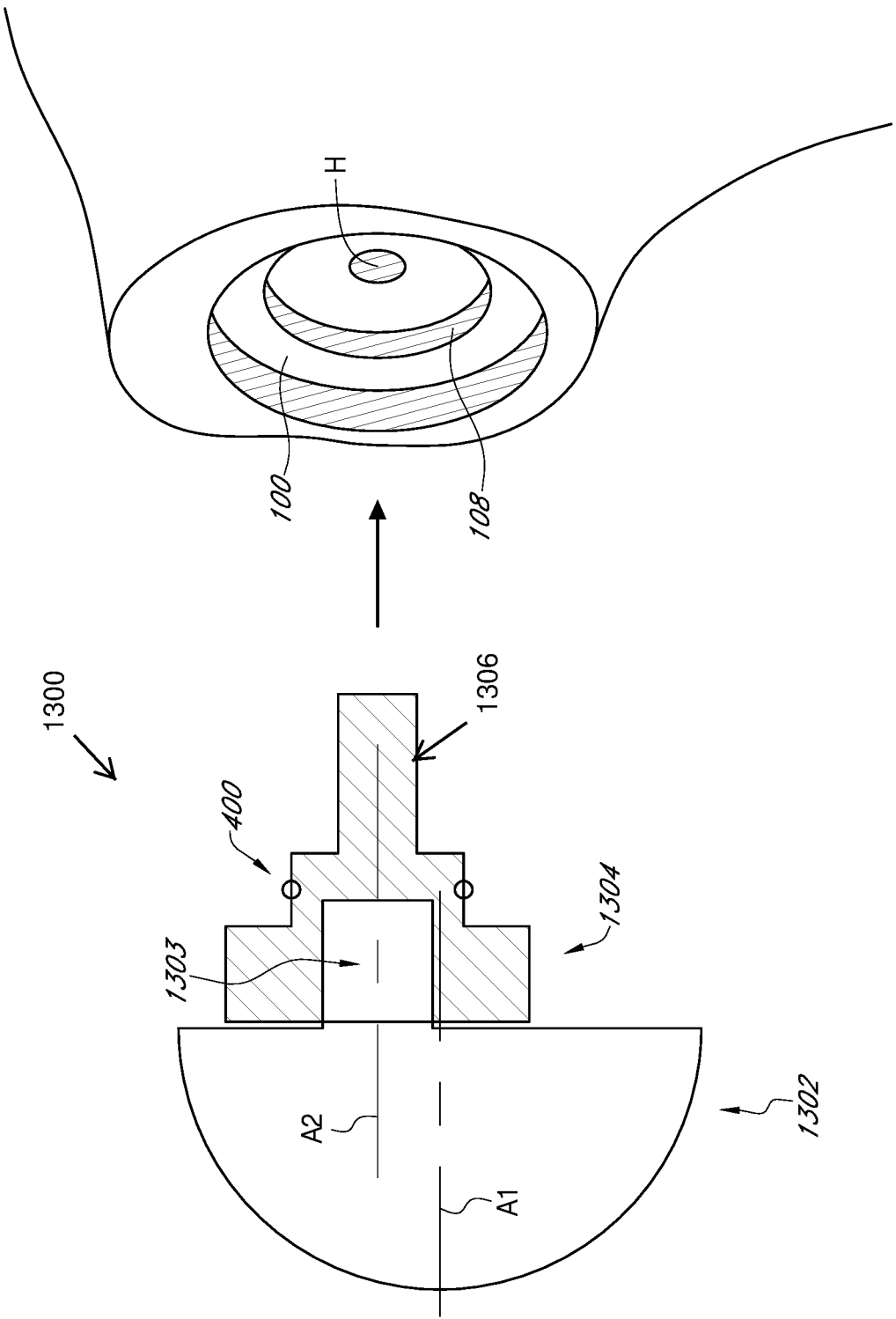
FIGS. 13A-13B, illustrates a method of implanting a replacement reverse prosthesis in the glenoid cavity, and mating the prosthesis with the implanted fixation ring.
Figure 13B:
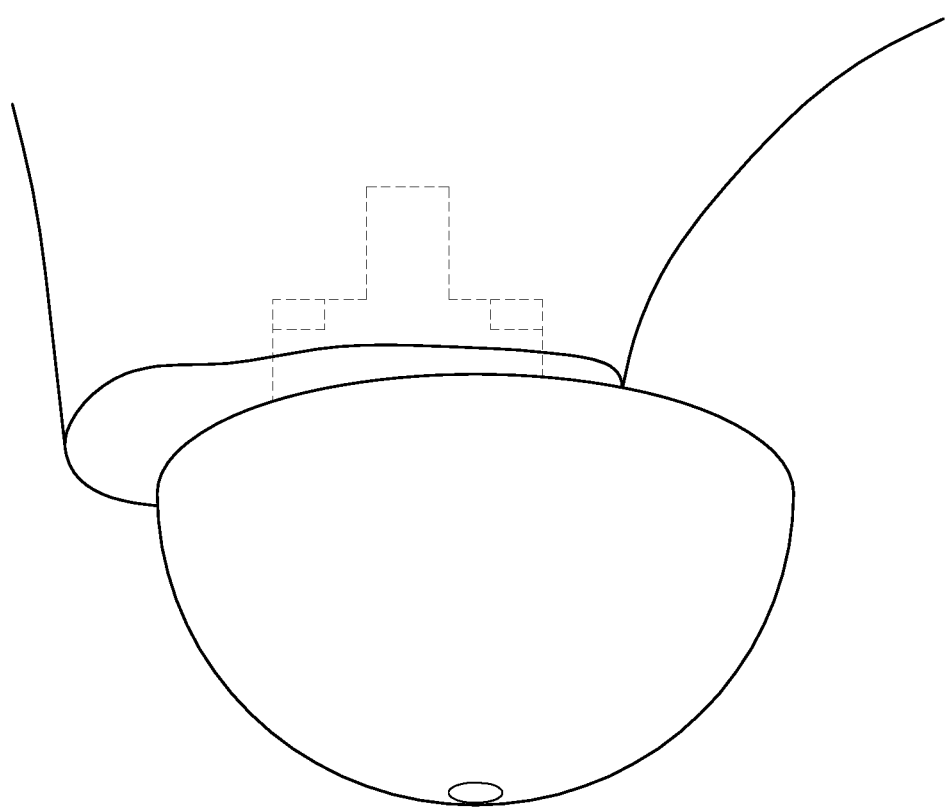

As shown in FIG. 13A, in some embodiments, an implant such as a disc, e.g., a metallic disc (e.g., as shown in FIGS. 7-9 for example) can then be placed into the previously implanted fixation ring 100 including a groove 108 configured to fit a new snap ring 400 as previously described. The implant 1300 can include a glenosphere 1302 with an offset peg 1303 configured to fit with baseplate 1304 with shaft 1306 (schematically shown in section view), and snap ring 400. The baseplate can have a longitudinal axis A2 that is offset from the longitudinal axis of the glenosphere A1 in some embodiments. FIG. 13B illustrates the reverse implant assembled and deployed within the glenoid cavity. Methods as disclosed herein can have several non-limiting potential advantages, including the following:
  1. an outer diameter adapted to provide for a snap ring fit between the disc and annular ring in the same manner as the PE component and the annular ring;
  2. a peg, pin, screw or other fixation means which is adapted to fit deeper into the central portion of the glenoid fossa to provide additional fixation means,
  3. a central tapered hole into which a reverse ball articulating component can be placed and rigidly fixed; and
  4. several peripheral holes through which screws can be driven to further increase the rigidity of fixation between the fixation disc and bone.

Following the removal of the anatomic, e.g., PE component, the surgeon can further prepare the glenoid fossa for the reverse fixation disc by drilling a centrally positioned hole. The hole can be adapted to receive a pin, post, screw, or other feature which is integrally attached to the medial aspect of the fixation disc. As the fixation disc can be positioned within the annular ring, the central fixation protrusion can be positioned within this hole in the glenoid bone such that further fixation rigidity is obtained.

Following the placement of the fixation disc in the annular ring, the surgeon can drill additional holes in the glenoid bone through peripheral holes in the fixation disc, which provides the ability to drive fixation screws through the fixation disc into the glenoid bone, even further improving rigidity, in addition to providing rotational stability. Due to the size constrains of the components, it can be advantageous to design the annular ring in a fashion that provides sufficient clearance through which these fixation screws can pass. To this end, the annular ring can be designed such that at on its periphery are several (four) indents of circular shape that provides clearance for passing of the peripheral screws.

Once the fixation disc is well fixed to the glenoid bone, the spherical articular component is introduced to the fixation disc. On its medial aspect, the articular component can have a cone-shaped protrusion which can be adapted to fit rigidly into a cone shaped hole centrally located within the fixation disc. This can provide a rigid fixation means by which the articular component is fixed to the fixation components using a technique and mechanism well known in the art.

Some embodiments of the modular, convertible shoulder system as disclosed for example herein can include several unique advantages not considered elsewhere, including but not limited to one or more of the following:
  The use of an annular fixation ring can further improve the fixation potential of inset glenoid technology as described herein. The ring can increase the rigidity of the overall PE glenoid construct, reducing its deflection under load, and improves fixation rigidly.
  The outer aspect of the annular ring can provide a surface which adheres to bone biologically and mechanically which provides further improvement of the rigidity of the fixation over time and in response to load in consideration of Wolf's law.
  This improved rigidity and fixation can be provided with no sacrifice of the 3 mm minimum material thickness of the PE component, so that joint mechanics can be maintained with no change in the overall stack height of the anatomic prosthesis.

The attachment mechanism between the PE articular and annular ring can be reversible in situ, meaning the PE component can be removed from the annular ring which the ring remains in the bone, and can be performed in a manner which is nondestructive to the ring or the surrounding bone.

The annular ring can be shaped so as to provide a receptacle into which a reverse articulation can be inserted and rigidly fixed.

The ring can provide clearance so that further rigidity can be obtained by passing screws through the reverse fixation disc, annular ring, and bone.

The fixation disc can provide a female receptacle into which the articular sphere's attachment post can be positioned. Providing a female receptacle is shown in some cases to be an easy surgical technique and very robust attachment mechanism.

Various other modifications, adaptations, and alternative designs are of course possible in light of the above teachings. Therefore, it should be understood at this time that within the scope of the appended claims the invention may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "insetting an implant into a glenoid cavity" includes "instructing the insetting of an implant into the glenoid cavity." The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A shoulder implant configured for implantation within a glenoid of a patient, the shoulder implant comprising:
   a cylindrical section having a central axis and comprising an articulating surface adapted to articulate with a complimentary component;
   a fixation ring positioned medial to the cylindrical section and disposed concentrically on the central axis, the fixation ring having an outer diameter smaller than an outer diameter of the cylindrical section, and an inner diameter defining a continuous circular opening at the medial end of the fixation ring, wherein a peripheral edge of the fixation ring comprises a groove; and
   a fixation element configured to contact bone of the patient and extending medially with respect to the fixation ring, disposed concentrically on the central axis, and having a cylindrical shape and an outer diameter located within the medial end of the fixation ring that is smaller than the inner diameter of the fixation ring to form a gap between an outside surface of the fixation element and an inside surface of the fixation ring at the medial end of the fixation ring, the fixation element comprising a circumferential channel extending about a circumference of the fixation element from the peripheral edge of the fixation element towards the central axis.

2. The shoulder implant of claim 1, wherein the cylindrical section is made of polyethylene.

3. The shoulder implant of claim 1, wherein the fixation element comprises a post or a peg.

4. The shoulder implant of claim 1, wherein the fixation element comprises one or more fins.

5. The shoulder implant of claim 1, wherein the fixation element is coaxially aligned with a central axis of the shoulder implant.

6. The shoulder implant of claim 1, wherein the groove is configured to house a snap ring.

7. The shoulder implant of claim 1, wherein the outer diameter of the fixation ring is 5-50% less than the outer diameter of the cylindrical section.

8. The shoulder implant of claim 1, wherein the fixation ring comprises a peripheral edge, the peripheral edge comprising a plurality of spaced apart radially inward indents.

9. The shoulder implant of claim 1, wherein the shoulder implant is configured to be inset when implanted.

10. The shoulder implant of claim 1, wherein the articulating surface is concave.

11. The shoulder implant of claim 1, wherein the articulating surface is convex.

12. The shoulder implant of claim 1, wherein the cylindrical section, the fixation ring, and the fixation element each have a cylindrical shape.

13. The shoulder implant of claim 1, wherein the cylindrical section, the fixation ring, and the fixation element are coaxially aligned.

14. The shoulder implant of claim 1, further comprising an osteoinductive or osteoconductive surface.

15. The shoulder implant of claim 1, wherein the fixation element is configured to facilitate bone ingrowth.

16. The shoulder implant of claim 1, wherein a thickness of the fixation element is greater than a thickness of the fixation ring.

17. The shoulder implant of claim 1, wherein a thickness of the fixation element is greater than a thickness of the cylindrical section.

* * * * *